US008955102B1

(12) United States Patent
Harding et al.

(10) Patent No.: US 8,955,102 B1
(45) Date of Patent: Feb. 10, 2015

(54) SYSTEM, METHOD AND COMPUTER PROGRAM PRODUCT FOR CONTROLLING ACCESS TO PROTECTED PERSONAL INFORMATION

(75) Inventors: Lari Harding, Clemmons, NC (US); Scott Renegar, Clemmons, NC (US); Angela Murray, Huntsville, TX (US)

(73) Assignee: Inmar, Inc., Winston-Salem, NC (US)

( * ) Notice: Subject to any disclaimer, the term of this patent is extended or adjusted under 35 U.S.C. 154(b) by 744 days.

(21) Appl. No.: 13/152,592

(22) Filed: Jun. 3, 2011

(51) Int. Cl.
*G06F 12/00* (2006.01)

(52) U.S. Cl.
USPC ........... 726/21; 726/2; 726/4; 726/17; 726/27

(58) Field of Classification Search
CPC ........ G06F 21/00; G06F 21/6218; G06F 7/04
USPC ...................................................... 726/2, 21
See application file for complete search history.

(56) References Cited

U.S. PATENT DOCUMENTS

| 2006/0248468 | A1 | 11/2006 | Constantine et al. | |
| 2010/0185871 | A1* | 7/2010 | Scherrer et al. | 713/186 |
| 2011/0030067 | A1 | 2/2011 | Wilson | |
| 2011/0134470 | A1* | 6/2011 | Naito | 358/1.15 |

OTHER PUBLICATIONS

Medstory Help Center, Search Results, (F) Health and Research Tabs, www.medstory.com/help/index.html, 2006.
excelbanter.com, Using a Toggle Button to Show or Hide Information in Several Cells, www.excelbanter.com/showthread.php?t=168912, Dec. 2007.

* cited by examiner

Primary Examiner — Baotran N To
(74) Attorney, Agent, or Firm — Myers Bigel Sibley & Sajovec, PA

(57) ABSTRACT

A computer-based system, method and computer program product for controlling access to protected personal information is disclosed. Protected personal information that is accessible by an information management application program is stored in a computer memory. In response to a request from an authenticated user for information, which includes protected personal information, information is displayed indicating that user has requested protected personal information, but the protected personal information is not displayed. In response to receiving user input requesting access to the protected personal information, a determination is made as to whether the user is authorized to access the requested protected personal information. If so, requested protected personal information is displayed to the user and information is stored relating to the user's access to protected personal information. Otherwise, requested protected personal information is not displayed to the user and information relating to the user's access to protected personal information is not stored.

14 Claims, 13 Drawing Sheets

FIG. 2A

| Carriers | Claims | Cash | Administration | My Profile |

FindView ⟵ 250

PHI [ON] ⟵ 205

[Search] [WIP]

Date Range (mm/dd/yyyy)    Status                          ● Single Rx  ○ Multiple Rx
[Fill Date ▶] [ ] to [ ]   [<All> ▶]

Cardholder ID              Name (at least 5 chars) ⟵ 215   Original AR Amount
[          ] ⟵ 210         [SMITH]                         [ ] to [ ]

NDC                        Group                           Open Dollar Range
[          ]               [     ]                         [ ] to [ ]

NPI                        Tag                             User Flags
[          ]               [<All Claims> ▶]                [<All Claims> ▶]

NCPDP                      Store                           Store Group
[          ]               [<All> ▶]                       [<All> ▶]

Application Type           Claim Application Exception Type   Claim Application Exception Category
[<All> ▶]                  [<All Claims> ▶]                    [<All Categories> ▶]

● All Carriers  ○ Selected Carriers    ● All Plans  ○ Selected Plans

[VIEW]

*FIG. 2B*

| | | | | | | | | | Carriers | Claims | Cash | Administration | My Profile | | | | |

PHI [OFF] — 305

31 of 31

List View

View results by: [Carrier Name ▼] [Store ▼]    [EXPORT] — 320

| | Rx# | Cardholder ID Name | Carrier Name | COB | Store NDC | Store | Fill Date | Claimed | Open | Write Off to Multi GLs |
|---|---|---|---|---|---|---|---|---|---|---|
| ☐ | 2264081 | | Aetna | 0 | 024 | 00078043105 | 10/01/2009 | $118.93 | 37.18 | ○ |
| ☐ | 4531131 | | Aetna | 0 | 067 | 00378531001 | 10/16/2009 | $11.20 | $11.20 | ○ |
| ☐ | 6037351 | | Aetna | 0 | 055 | 00088222060 | 09/01/2009 | $164.81 | $164.81 | ○ |
| ☐ | 6037351 | | Aetna | 0 | 055 | 00088222060 | 10/09/2009 | $163.98 | $163.98 | ○ |

*FIG. 3A*

| Rx# | Cardholder ID | Name | Carrier Name | COB | Store | Store NDC | Fill Date | Claimed | Open | Write Off to Multi Gts |
|---|---|---|---|---|---|---|---|---|---|---|
| 2264081 | W168681897 | JONES, ROBERT | Aetna | 0 | 024 | 00078043105 | 10/01/2009 | $118.93 | 37.18 | ○ |
| 4531131 | W101139607 | DAVIS, ANN | Aetna | 0 | 067 | 00378531001 | 10/16/2009 | $11.20 | $11.20 | ○ |
| 6037351 | W157835488 | SMITH, JOHN | Aetna | 0 | 055 | 00088222060 | 09/01/2009 | $164.81 | $164.81 | ○ |
| 6037351 | W157835488 | SMITH, JOHN | Aetna | 0 | 055 | 00088222060 | 10/09/2009 | $163.98 | $163.98 | ○ |

*FIG. 3B*

| PHI OFF | Carriers | Claims | Cash | Contracts | Admin |
|---------|----------|--------|------|-----------|-------|

Detail

Rx 2000443  Status: Open

| Status: | Open | Name: | | Claimed: | $17.64 |
|---|---|---|---|---|---|
| Fill Date: | 4/5/2010 | Cardholder ID: | | Open: | $17.64 |
| Sold Date: | 4/5/2010 | Medical Record #: | | Co-pay: | |
| Transmitted Date: | 4/5/2010 | Patient Relationship: | 0 | Transaction Price: | $17.64 |
| Date Written: | 4/5/2010 | Patient DOB: | 5/27/2010 | Dispensing Fee: | $2.00 |
| Carrier: | Aetna 1 | Patient Sex: | M | Acquisition Cost: | $4.23 |
| Plan: | Aetna PA | Authorization: | 300010930622266 | Ingredient Cost Sub: | |
| Plan Code: | AETPA | Manual Bill: | N | Usual & Customary: | $29.84 |
| Group: | | Prescriber NPI: | | Tax: | |
| Transaction Code: | 0019395 | Prescriber DEA: | BT0526131 | Refill: | 0 |
| Claim Reference #: | 49059180 | Prescriber Name: | TALAMO, ROBERT J. | Refills Remaining: | 0.00 |
| NDC: | 00555097302 | Generic Flag: | Y | DAW: | 0 |
| GCN: | 5001 | Generic Indicator: | 1 | COB: | 0 |
| Pack Size: | 100.000 | Brand/Generic: | Generic | OIC: | |
| PCN: | | Preferred Drug: | | Diagnosis Code: | |
| Patient Address: | | | | Days Supply: | 30 |
| | | | | Quantity Dispensed: | 30.0000 |

FIG. 4A

| PHI ON | | | | | |
|---|---|---|---|---|---|
| | Carriers | Claims | Cash | Contracts | Admin |
| | | Detail | | | |

Rx 2000443   Status: Open

| | | | |
|---|---|---|---|
| Status: | Open | Name: | Smith, John |
| Fill Date: | 4/5/2010 | Cardholder ID: | 123344550 |
| Sold Date: | 4/5/2010 | Medical Record #: | 1234567 |
| Transmitted Date: | 4/5/2010 | Patient Relationship: | 3 |
| Date Written: | 4/5/2010 | Patient DOB: | 5/27/2010 |
| Carrier: | Aetna 1 | Patient Sex: | M |
| Plan: | Aetna PA | Authorization: | 30001093062266 |
| Plan Code: | AETPA | Manual Bill: | N |
| Group: | | Prescriber NPI: | |
| Transaction Code: | 0019395 | Prescriber DEA: | BT0526131 |
| Claim Reference #: | 49059180 | Prescriber Name: | TALAMO, ROBERT J. |
| NDC: | 00555097302 | Generic Flag: | Y |
| GCN: | 5001 | Generic Indicator: | 1 |
| Pack Size: | 100.000 | Brand/Generic: | Generic |
| PCN: | | Preferred Drug: | |
| Patient Address: | 1234 Main St | | |
| | Anywhere, NC 27000 | | |

| | |
|---|---|
| Claimed: | $17.64 |
| Open: | $17.64 |
| Co-pay: | |
| Transaction Price: | $17.64 |
| Dispensing Fee: | $2.00 |
| Acquisition Cost: | $4.23 |
| Ingredient Cost Sub: | |
| Usual & Customary: | $29.84 |
| Tax: | |
| Refill: | 0 |
| Refills Remaining: | 0.00 |
| DAW: | 0 |
| COB: | |
| OIC: | 325.46 |
| Diagnosis Code: | |
| Days Supply: | 30 |
| Quantity Dispensed: | 30.0000 |

PHI OFF

| | A | B | C | D | E | F | G | H | I | J | K |
|---|---|---|---|---|---|---|---|---|---|---|---|
| | RX # | Cardholder ID | Name | Carrier Name | Plan Code | COB | Store | NPI | NCPDP | NDC | NDC Description |
| 1 | 22222222 | | | Catalyst RX | CATRX | 0 | 014 | 1588393967 | 2132316 | 0055097302 | AMPHETAMINE SALTS 20 MG TABLET |
| 2 | 22222222 | | | Catalyst RX | CATRX | 0 | 014 | 1588393967 | 2132316 | 59417010310 | VYVANCE 30 MG CAPSULE |
| 3 | 22222222 | | | Catalyst RX | CATRX | 0 | 014 | 1588393967 | 2132316 | 00078044005 | RITALIN 10 MG TABLET |

PHI ON

| | A | B | C | D | E | F | G | H | I | J | K |
|---|---|---|---|---|---|---|---|---|---|---|---|
| | RX # | Cardholder ID | Name | Carrier Name | Plan Code | COB | Store | NPI | NCPDP | NDC | NDC Description |
| 1 | 22222222 | MD000666401 | OJHGNNELL, DJKGEL | Catalyst RX | CATRX | 0 | 014 | 1588393967 | 2132316 | 0055097302 | AMPHETAMINE SALTS 20 MG TABLET |
| 2 | 22222222 | MD000668801 | SHKJHGER, CLJHGE | Catalyst RX | CATRX | 0 | 014 | 1588393967 | 2132316 | 59417010310 | VYVANCE 30 MG CAPSULE |
| 3 | 22222222 | MD888868301 | SHKJHGER, MKJHORIE | Catalyst RX | CATRX | 0 | 014 | 1588393967 | 2132316 | 00078044005 | RITALIN 10 MG TABLET |

510 / 515

Created On: 04/19/2010
Report Filters: Client=7770, System Data Range: 03/01/2010 to 03/31/2010; Users: All; Carrier: All Carriers, Plan Code=All, All NDCs; Store Group=All, Carrier Groups=On

600

605
610
615

| User ID | User Name | View Access | Date & Time Stamp | Application | Carrier Code | Carrier Name | Plan Code | Plan |
|---|---|---|---|---|---|---|---|---|
| mangel | Mary Angel | Custom report | 3/1/2010 08:00AM | Spectrum | 1007 | Argus | ARGFSC | ARGfutscrip |
| mangel | Mary Angel | Custom report | 3/10/2010 10:00AM | Spectrum | 1002 | Argus | AETPA | Aetna PA |
| mangel | Mary Angel | Claims Application Exceptions | 3/11/2010 09:00AM | Spectrum | 1007 | Argus | ARGFSC | ARGfutscrip |

| Group | Rx # | Fill Date | NDC | NDC Description | COB | Days Supply | Qty Dispensed | Transaction Code | Cardholder ID | Name |
|---|---|---|---|---|---|---|---|---|---|---|
| AB12345 | 2000442 | 04/05/2010 | 59417010510 | PLAVIX 75 MG TABLET | 0 | 30 | 30 | B | abc123456789 | DAVIS, JILL |
| AB12346 | 2000443 | 04/05/2010 | 00555097302 | LIPITOR 20 MG TABLET | 0 | 30 | 30 | B | 6789123456 | SMITH, JANE |
| AB12347 | 2000444 | 04/05/2010 | 00555078702 | LIPITOR 40 MG TABLET | 0 | 90 | 90 | B | 123654789 | SMITH, JOHN |

| Patient Address | Medical Record # | Relationship | Date Of Birth | Patient Sex | Diagnosis Code | Store Group | Store ID | NPI | NCPDP |
|---|---|---|---|---|---|---|---|---|---|
| 123 Main St., Anywhere, US 12345 | 9988776655 | 3 | 10/08/1996 | F | 543 | GROUP A | 043 | 1700110467 | 3992674 |
| 123 Main St., Anywhere, US 12345 | 9988776655 | 3 | 05/27/1989 | F | 544 | GROUP A | 043 | 1700110467 | 3992674 |
| 123 Main St., Anywhere, US 12345 | 9988776655 | 3 | 02/09/1988 | M | 545 | GROUP A | 043 | 1700110467 | 3992674 |

*FIG. 6*

PHI Activation Report

Created By: mangel On: 04/19/2010
Report Filters: Client=7770, System Date Range: 03/01/2010 to 03/31/2010; Users: mangel;

| User ID | User Name | PHI On | PHI Off | Session ID |
|---------|-----------|--------|---------|------------|
| mangel | Mary Angel | 03/01/2010 08:00AM | 03/01/2010 08:40AM | 123456789 |
| mangel | Mary Angel | 03/10/2010 10:00AM | 03/10/2010 10:05AM | 234567890 |
| mangel | Mary Angel | 03/11/2010 09:00AM | 03/11/2010 09:20AM | 345678901 |
| mangel | Mary Angel | 03/19/2010 08:30AM | 03/19/2010 09:45AM | 456789012 |

*FIG. 7*

SYSTEM, METHOD AND COMPUTER PROGRAM PRODUCT FOR CONTROLLING ACCESS TO PROTECTED PERSONAL INFORMATION

FIELD OF THE INVENTION

The present invention generally relates to a computer-based system, method and computer program product for controlling access to protected personal information, and to logging and storing information about access to protected personal information.

BACKGROUND OF THE INVENTION

Numerous federal, state and local laws, regulations and rules protect the privacy and security of personal information, particularly, health information. For example, federal laws limit access to health information to treatment, payment and health care operations personnel only to the minimum extent necessary to accomplish the intended purpose. Certain health information is "protected health information" (PHI), such as, name, address and Social Security number, and may not be disclosed to unauthorized personnel. In addition, information about access to protected health information must be logged and stored for significant periods of times, and unauthorized access to protected health information may have to be reported to legal and regulatory authorities.

Information management application programs, such as information management programs used to process health care and pharmaceutical insurance claims, require access to protected personal information, such as protected health information. Such insurance claim information management application programs may be accessed by many different users. Some users will require constant access to protected health information, while others require only infrequent access and still others will need no access to protected health information.

Known systems and methods for controlling access to protected personal information establish and assign user roles and only certain user roles are authorized to access protected health information. Known systems log and store information about all information accessed by such authorized users even though the authorized user may not always need access to protected health information, which increases the cost of compliance with laws regulating access to protected health information. Thus, what is needed is a computer based system and method and computer program product for controlling access to protected personal information and that minimizes the amount of protected personal information that must be logged and stored for legal or other reasons.

BRIEF DESCRIPTION OF THE DRAWINGS

FIGS. 2A and 2B are diagrams illustrating a user interface for searching for and controlling the display of protected personal information according to an embodiment of the present invention.

FIGS. 3A and 3B are diagrams illustrating a user interface for displaying protected personal information according to an embodiment of the present invention.

FIGS. 4A and 4B are diagrams illustrating a user interface for displaying protected personal information according to another embodiment of the present invention.

FIGS. 5A and 5B are exemplary reports containing protected personal information generated by a computerized system for controlling access to protected personal information according to an embodiment of the present invention.

FIG. 6 is an exemplary report containing information about access to protected personal information generated by a computerized system for controlling access to protected personal information according to an embodiment of the present invention.

FIG. 7 is an exemplary report containing information about activating and de-activating access to protected personal information generated by a computerized system for controlling access to protected personal information according to an embodiment of the present invention.

DETAILED DESCRIPTION OF PREFERRED EMBODIMENTS

Reference will now be made in detail to the presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention cover such modifications and variations as come within the scope of the appended claims and their equivalents.

Figure 1:
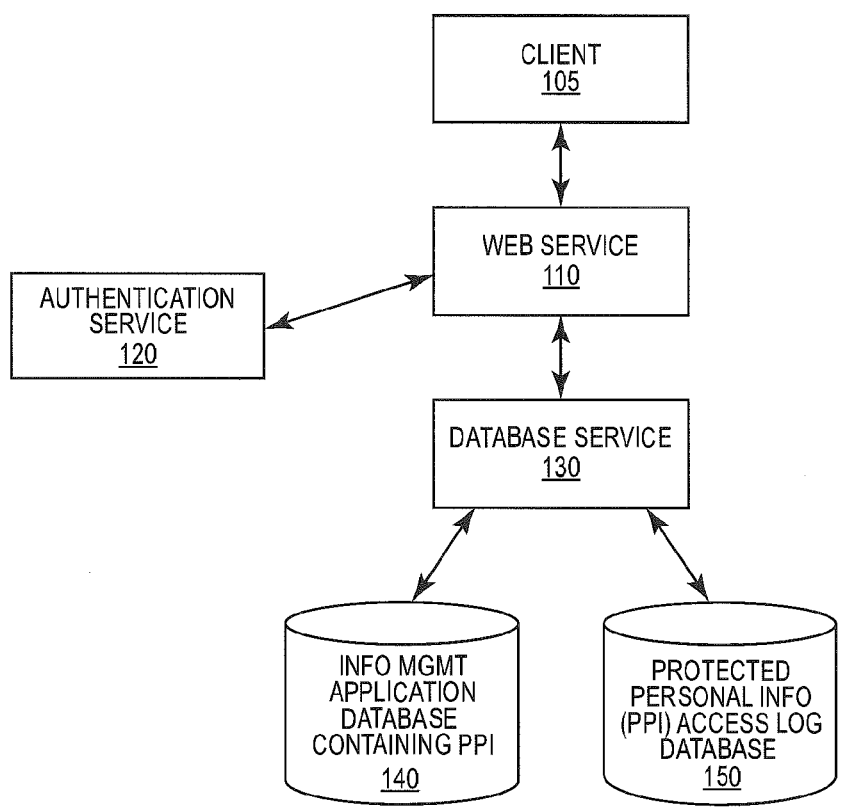
FIG. 1 is a diagram illustrating a computerized system for controlling access to protected personal information according to an embodiment of the present invention.

FIG. 1 is a diagram of a system 100 for controlling access to protected personal information according to an exemplary embodiment of the present invention. As can be seen in FIG. 1, a client computer program 105, such as a web browser, is in electronic communication with a web service 110. A suitable browser may be Internet Explorer and a suitable web service may be Internet Information Services (IIS) running on a WINDOWS Server, all of which are available from Microsoft Corporation of Redmond, Wash.

A user of client program 105 may request, via a user interface, access to an information management application program, which includes protected personal information. An exemplary information management application program that includes protected personal information may be a health care information management application program, such as a health care or pharmaceutical insurance claim information management application program used by an insurance carrier for processing health care or pharmaceutical insurance claims. Examples of such insurance claim information management application programs include SPECTRUM and RX RECON, both available from Inmar of Winston-Salem, N.C. The invention, however, is not limited to any particular information management application program and can be used in connection with any information management application program that provides access to protected personal information.

Protected personal information includes personal information that is protected from access and disclosure. In an embodiment, the present invention may be used to control access to health information, which is subject to various federal, state and local laws and regulations limiting access to certain health information, requiring logging and storing detailed information about access to certain health information and reporting instances of unauthorized access to or disclosure of certain health information.

In an embodiment, the invention can be used to control access to particular types of protected personal information, such as protected health information (PHI), as that term is defined by federal laws, regulations and rules. Items of protected health information may include one or more of the following information about a person: Name, Address, Social Security Number, Medical Record Number, and Cardholder Identifier. Protected health information also may include the following items of information, when combined with one or more of Name, Address, Social Security Number, Medical Record Number, and Cardholder Identifier information: Date of Birth, Sex, Relationship (to cardholder), Diagnosis Code, National Drug Code (NDC), NDC Description, Generic Code Number (GCN), GCN Description.

As discussed above, when protected personal information is accessed, information about the access of the protected personal information is logged and stored in a computer memory. In an embodiment, in addition to logging and storing information about access to the protected health information discussed above, one or more of the following items of information are also stored for use in connection with providing reports about access to protected health information: Information Viewed or Accessed (report/screen); Date and Time of View or Access, User Name, User Identifier, Application Program, Insurance Carrier Name, Insurance Carrier Identifier, Insurance Plan Name, Insurance Plan Identifier, Insurance Group, Store Group Identifier, National Council for Prescription Drug Programs (NCPDP) or National Provider Identifier (NPI), Quantity Dispensed, Days Supply, Prescription Number, Fill Date, Coordination of Benefits (COB).

The invention, however, is not limited to use in connection with health information that is regulated by law, such as protected health information. Rather, the invention can be used in connection with controlling and logging access to personal information used in any information management application program.

Returning to FIG. 1, user credentials, such as a user identifier and password, are transmitted from client program 105 to web service 110. Web service 110 requests authentication service 120 to authenticate the user. Such an authentication service may use Active Directory, available from Microsoft Corporation of Redmond, Wash., to define one or more security roles, which are discussed in more detail below, to allow or deny access to protected personal information and to protected personal information reporting services.

If the user has authorization to access the information management application program, the user is authenticated by authentication service 120, which transmits authentication information to web service 110. Authentication information is information indicating the user has been authenticated and authorized to access the information management application program. The web service 110 then transmits the authentication information to client program 105.

After a user has been authenticated, the user may transmit a request to access information via information management application program. The request is received by web service 110 and web service 110 in turn transmits the request to database service 130. A suitable database service is Microsoft SQL Server, which is available from Microsoft Corporation. Database service 130 requests information stored in a computer memory such as database 140 and receives the requested information from database 140. Database service 130 returns the requested information to web service 110, which transmits the information to client program 105.

As will be discussed in more detail below, if a user, via client program 105, makes an information request that includes protected personal information or desires to search based on an item of protected personal information, processing logic determines whether the user is authorized to access protected personal information. If a user is authorized to access protected personal information, in an embodiment, as a default, the protected personal information will not be displayed via client program 105, but the user may be provided, via client program 105, an option for providing input indicating that the user desires access to the requested protected personal information. In an embodiment, the option for providing input indicating that the user desires access to the requested protected personal information may be implemented as a button or a toggle, which will be discussed in more detail below. If a user is not authorized to access protected personal information, in an embodiment, the user is not provided an option for providing input indicating that the user desires access to the requested protected personal information.

If a user provides input indicating that the user desires access to the requested protected personal information, processing logic causes information a) indicating that a user provided input indicating that the user requested access to the requested protected personal information, and b) each item of protected personal information accessed by and/or displayed to the user to be logged and stored in protected personal information access log database 150. A suitable database for storing protected personal information access log information is an encrypted Microsoft SQL Server database available from Microsoft Corporation. The protected personal information access log information stored in database 150 also may be used in generating reports relating to access to protected personal information.

Figure 2A:
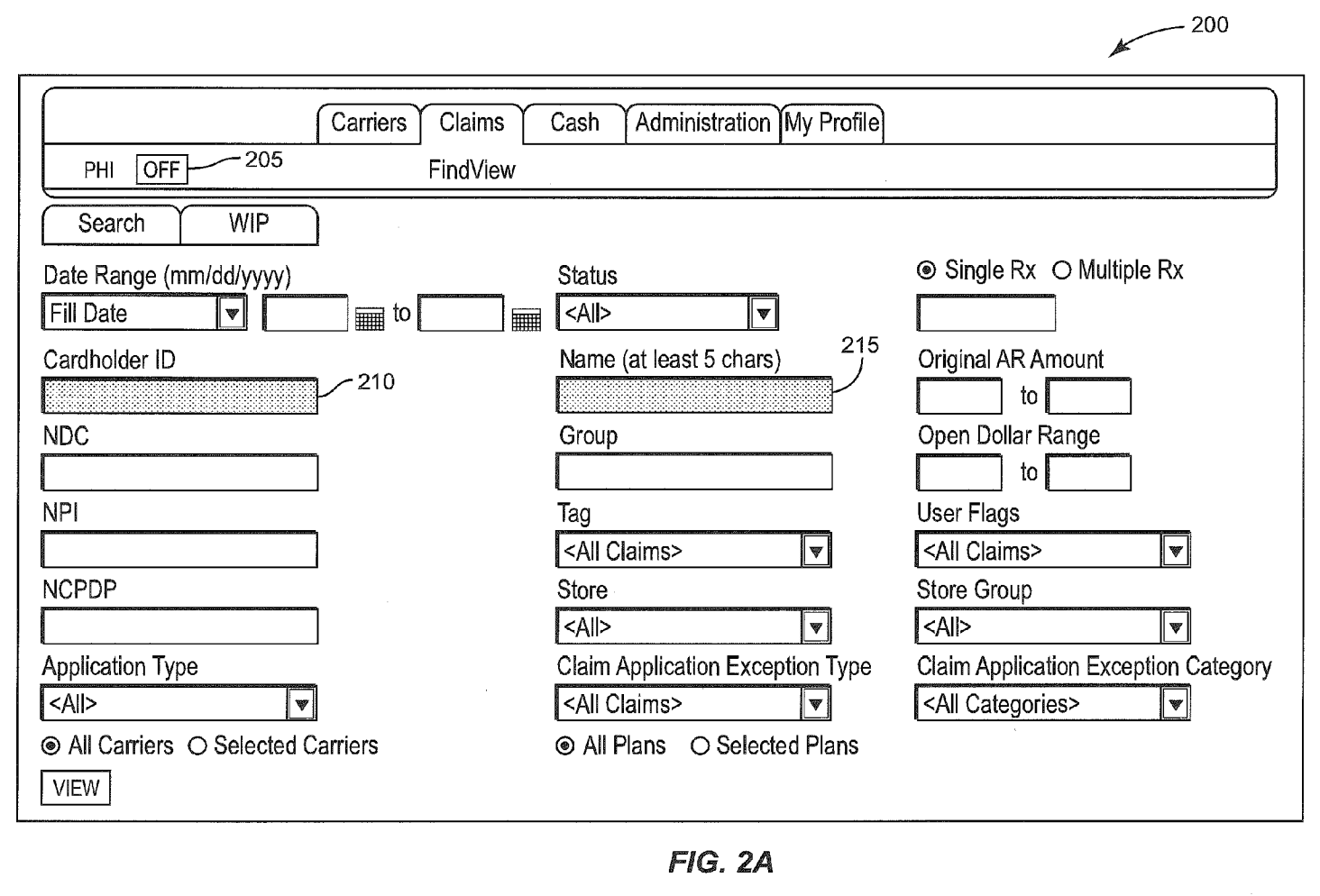

FIGS. 2A and 2B are diagrams illustrating a user interface for searching for and controlling the display of protected health information according to an embodiment of the present invention. Referring to FIG. 2A, interface 200 is an interface to an exemplary information management application program for processing insurance claims for pharmaceuticals. More specifically, interface 200 allows a user to search for one or more insurance claims. As can be seen from FIG. 2A, a PHI button, or toggle, 205 is provided for controlling access to protected health information. The term toggle is used to indicate any mechanism for switching between two states by receiving user input. A toggle may be implemented, for example, by displaying via a graphical user interface a button, which can be selected via an input device such as a computer mouse or keyboard.

In an embodiment, and as illustrated in FIG. 2A, the default setting for the PHI toggle 205 is "OFF." When the PHI toggle 205 is set to "OFF," certain items of protected health information are not displayed via interface 200 and cannot be used for search for insurance claims. For example, protected health information such as Cardholder ID 210 and Name 215 are not displayed when the PHI toggle 205 is set to "OFF." When the PHI toggle 205 is set to "OFF," information not consisting of protected health information is displayed via interface 200 and can be used to search for insurance claims. In an embodiment, items of information consisting of protected health information, such as Cardholder ID 210 and Name 215 may be grayed out and/or may not accept input via an input device.

As discussed above, a user can toggle the PHI toggle 205 between "OFF" and "ON" states by, for example, selecting a button via an input device, such as a computer mouse. When PHI toggle 205 is "OFF," the word "OFF" is displayed on the toggle 205. A preselected color, such as gray, also may be used to indicate the PHI toggle 205 is set to "OFF."

Referring to FIG. 2B, interface 250 is the same interface to an exemplary information management application program for processing insurance claims for pharmaceuticals as illustrated in FIG. 2A, but the PHI toggle 205 is set to "ON." When PHI toggle 205 is "ON," the word "ON" is displayed on the toggle 205. A preselected color, such as green, also may be used to indicate the PHI toggle 205 is set to "ON." As can be seen from FIG. 2B, when the PHI toggle 205 is set to "ON," protected health information is displayed and can be used to search for insurance claims via interface 250. For example, protected health information such as Cardholder ID 210 and Name 215 is displayed and can be used to search for insurance claims when the PHI toggle 205 is set to "ON." As in the case when the PHI toggle 205 is set to "OFF," when the PHI toggle 205 is set to "ON," information not consisting of protected health information is also displayed and can be used to search for insurance claims via interface 250.

FIGS. 3A and 3B are diagrams illustrating a user interface for displaying protected health information according to an embodiment of the present invention. Referring to FIG. 3A, interface 300 is an interface to an exemplary information management application program for processing insurance claims for pharmaceuticals. More specifically, interface 300 displays information about one or more insurance claims in a list view. As can be seen from FIG. 3A, a PPI button, or toggle, 305 is provided for controlling access to and the display of protected health information. In an embodiment, and as illustrated in FIG. 3A, the default setting for the PHI toggle 305 is "OFF." When the PHI toggle 305 is set to "OFF," certain items of protected health information are not displayed via interface 300 and cannot be used for search for insurance claims. For example, protected health information such as Cardholder ID 310 and Name 315 are not displayed when the PHI toggle 305 is set to "OFF." When the PHI toggle 305 is set to "OFF," information not consisting of protected health information is displayed via interface 300.

As discussed above, a user can toggle the PHI toggle 305 between "OFF" and "ON" settings by, for example, selecting the button via an input device, such as a computer mouse. When PHI toggle 305 is "OFF," the word "OFF" is displayed on the toggle 305. A preselected color, such as gray, also may be used to indicate the PHI toggle 305 is set to "OFF."

Referring to FIG. 3B, interface 350 is the same interface to an exemplary information management application program for processing insurance claims for pharmaceuticals as illustrated in FIG. 3A, but the PHI toggle 305 is set to "ON." When PHI toggle 305 is "ON," the word "ON" is displayed on the toggle 305. A preselected color, such as green, also may be used to indicate the PHI toggle 305 is set to "ON." As can be seen from FIG. 3B, when the PHI toggle 305 is set to "ON," protected health information is displayed via interface 350. For example, protected health information such as Cardholder ID 310 and Name 315 is displayed when the PHI toggle 305 is set to "ON." As in the case when the PHI toggle 305 is set to "OFF," when the PHI toggle 305 is set to "ON," information not consisting of protected health information is also displayed and can be used to search for insurance claims via interface 350.

FIGS. 4A and 4B are diagrams illustrating a user interface for displaying protected health information according to another embodiment of the present invention. Referring to FIG. 4A, interface 400 is an interface to an exemplary information management application program for processing insurance claims for pharmaceuticals. More specifically, interface 400 displays detailed information about such an insurance claim. As can be seen from FIG. 4A, a PPI button, or toggle, 405 is provided for controlling access to protected health information. In an embodiment, and as illustrated in FIG. 4A, the default setting for the PHI toggle 405 is "OFF." When the PHI toggle 405 is set to "OFF," protected health information is not displayed via interface 400. For example, protected health information such as Patient Address 410, Name 415, Cardholder ID 420 and Medical Record #425 is not displayed when the PHI toggle 405 is set to "OFF." Even when the PHI toggle 405 is set to "OFF," information not consisting of protected health information is displayed via interface 400.

In an embodiment, a user can toggle the PHI toggle 405 between "OFF" and "ON" settings by, for example, selecting the button via an input device, such as a computer mouse. When PHI toggle 405 is "OFF," the word "OFF" is displayed on the toggle 405. A preselected color, such as gray, also may be used to indicate the PHI toggle 405 is set to "OFF."

Referring to FIG. 4B, interface 450 is the same interface to an exemplary information management application program for processing insurance claims for pharmaceuticals as illustrated in FIG. 4A, but the PHI toggle 405 is set to "ON." When PHI toggle 405 is "ON," the word "ON" is displayed on the toggle 405. A preselected color, such as green, also may be used to indicate the PHI toggle 405 is set to "ON." As can be seen from FIG. 4B, when the PHI toggle 405 is set to "ON," protected health information is displayed via interface 450. For example, protected health information such as Patient Address 410, Name 415, Cardholder ID 420 and Medical Record Number 425 is displayed when the PHI toggle 405 is set to "ON." As in the case when the PHI toggle 405 is set to "OFF," when the PHI toggle 405 is set to "ON," information not consisting of protected health information is also displayed via interface 450.

In an embodiment, various levels of access to protected personal information can be established and assigned to users. For example, user roles may include PPI Administrator and PPI Access.

FIGS. 5A and 5B are reports generated by a computerized system for controlling access to protected health information according to an embodiment of the present invention. Returning to FIGS. 3A and 3B, interfaces 300 and 350 each include an export button 320. When a user selects export button 320 via an input device such as a computer mouse, reports are generated, the content of which is illustrated in FIGS. 5A and 5B. The export button 320 can be used, for example, to export the information being displayed via interfaces 300, 350 to another application, such as a spreadsheet application, or to create a PDF file containing the information displayed via interfaces 300 and 350. Specifically referring to FIG. 5A, a report generated by a system for controlling access to protected health information according to an exemplary embodiment of the present invention is shown. The report shown in FIG. 5A is generated by selecting the export button 320, as shown in FIG. 3A. As also shown in FIG. 3A, the PHI toggle 305 is set to "OFF." Thus, the report 500, which was generated when the PHI toggle was set to "OFF," does not include items of protected health information, such as Cardholder ID 510 and Name 515. The report shown in FIG. 5B is generated by selecting the export button 320, as shown in FIG. 3B. As also shown in FIG. 3B, the PHI toggle 305 is set to "ON." Thus, the report 550, which was generated when the PHI toggle was set to "ON," does include items of protected health information, such as Cardholder ID 510 and Name 515.

In an embodiment, for users assigned either a PPI Administrator or PPI Access role, when authenticated by the information management application program, a PPI toggle is visible and selectable by the user, but is set to "OFF" as a default. If the PPI toggle is set to "ON" by the user, information indicating that the PPI toggle was activated by the user will be logged and stored in a computer memory. If the PPI toggle is set to "ON," such users will have access to protected personal information on screens displayed and reports generated by the information management application program, as well as search filters, which are discussed in more detail below. If the PPI toggle is set to "ON," any protected personal information accessed by the user, and information relating to the user's access to the protected personal information is logged and stored in a computer memory. If the PPI toggle is set to "OFF" by the user, information indicating that the PPI toggle was de-activated by the user will be logged and stored in a computer memory. If the PPI toggle is set to "OFF," such users will not have access to protected personal information on screens displayed and reports generated by the information management application program, as well as search filters, which are discussed in more detail below. If the PPI toggle is set to "OFF," no information accessed by the user while the PPI toggle is set to "OFF" is logged and stored in a computer memory. Users assigned the PPI Administrator role will have access to reports regarding access to protected personal information and the activation/de-activation of the PPI toggle, which are discussed in more detail below. Users assigned the PPI Access role will not have access to such reports.

In an embodiment, for users not assigned either a PPI Administrator or PPI Access role, when authenticated by the information management application program, a PPI toggle is visible but disabled and therefore not selectable by such a user. Such users will not have access to protected personal information on screens displayed and reports generated by the information management application program, as well as search filters. No information accessed by such a user is logged and stored in a computer memory.

In an embodiment, if a PPI toggle is set to "ON," and a search is performed, protected personal information is returned and displayed to the user. If, while the protected personal information is displayed, the PPI toggle is then set to "OFF," the protected personal information that was returned from the original search will still be displayed until a new search is performed. Alternatively, if, while the protected personal information is displayed, the PPI toggle is then set to "OFF," the protected personal information that was returned from the original search will no longer be displayed as soon as the PPI toggle is set to "OFF."

Similarly, if a PPI toggle is set to "OFF," and a search is performed, protected personal information is not returned and displayed to the user. If, the PPI toggle is then set to "ON," protected personal information will still not be displayed until a new search is performed. Alternatively, if a PPI toggle is set to "OFF," and a search is performed, protected personal information is not returned and displayed to the user. If, the PPI toggle is then set to "ON," the protected personal information will immediately be displayed.

In another embodiment, the system of the present invention may present a user with an option to save search results or a report containing protected personal information or a report template for displaying protected personal information via a computer display. If such search results, report or template are saved while the PPI toggle is set to "ON," and a user then attempts to retrieve such search results, report or template while the PPI toggle is still set to "ON," the search results, report or template that will be displayed will include protected personal information. Information regarding a user's access to such stored search results, report or template containing protected personal information is also logged and stored. Conversely, if a user attempts to retrieve such saved search results, report or template while the PPI toggle is set to "OFF," or if the user is no longer authorized to access protected personal information, a message may be displayed indicating that the saved search results, report or template that was requested previously included protected personal information but no longer does, and the saved search results, report or template will be modified so as not to display protected personal information that was contained in the previously saved search results, report or template. In this case, information regarding the user's attempt to access saved search results, report or template is not logged and stored. Alternatively, if a user attempts to retrieve such saved search results, report or template while the PPI toggle is set to "OFF," or if the user is no longer authorized to access protected personal information, the saved search results, report or template may display the protected personal information that was contained in the previously saved search results, report or template. In this case, information regarding the user's to access saved search results, report or template is logged and stored.

FIG. 6 is an exemplary report containing information about access to protected personal information generated by a computerized system for controlling access to protected personal information according to an embodiment of the present invention. As can be seen from FIG. 6, the report 600 contains information about protected personal information accessed by a particular user during a particular time period. More specifically, report 600 indicates that protected personal information was accessed by a particular user on three (3) separate occasions during the time period specified for the report.

Each row of information 605, 610 and 615 represents an instance when protected personal information was viewed or accessed by the user. Each row 605, 610 and 615 includes one or more of the following items of information regarding access to protected personal information: User Identifier, User Name, Information Viewed or Accessed, Data and Time, Application, Insurance Carrier Code, Insurance Carrier Name, Insurance Plan Code, Insurance Plan Name, Insurance Group, Prescription Number, Fill Date, NDC, NDC Description, COB, Days Supply, Quantity Dispensed, Transaction Code, Cardholder Identifier, Patient Name, Patient Address, Social Security Number, Medical Record Number, Relationship, Date of Birth, Patient Sex, Diagnosis Code, Store Group, Store Identifier, NPI and NCPDP.

FIG. 7 is an exemplary report containing information about activating and de-activating access to protected personal information generated by a computerized system for controlling access to protected personal information according to an embodiment of the present invention. As can be seen from FIG. 7, the report 700 contains information about activation and de-activation of protected personal information by a particular user during a particular time period. More specifically, report 700 contains four (4) rows of information 705, 710, 715 and 720, which indicates that access to protected personal information was activated by a particular user on four (4) separate occasions during the time period specified for the report.

Each row of information 705, 710, 715 and 720 represents an instance when access to protected personal information was activated by the user and includes the following items of information regarding activating access to protected personal information: User Identifier, User Name, Data and Time when access to protected personal information was Activated and De-activated, and a Session Identifier.

Figure 8:
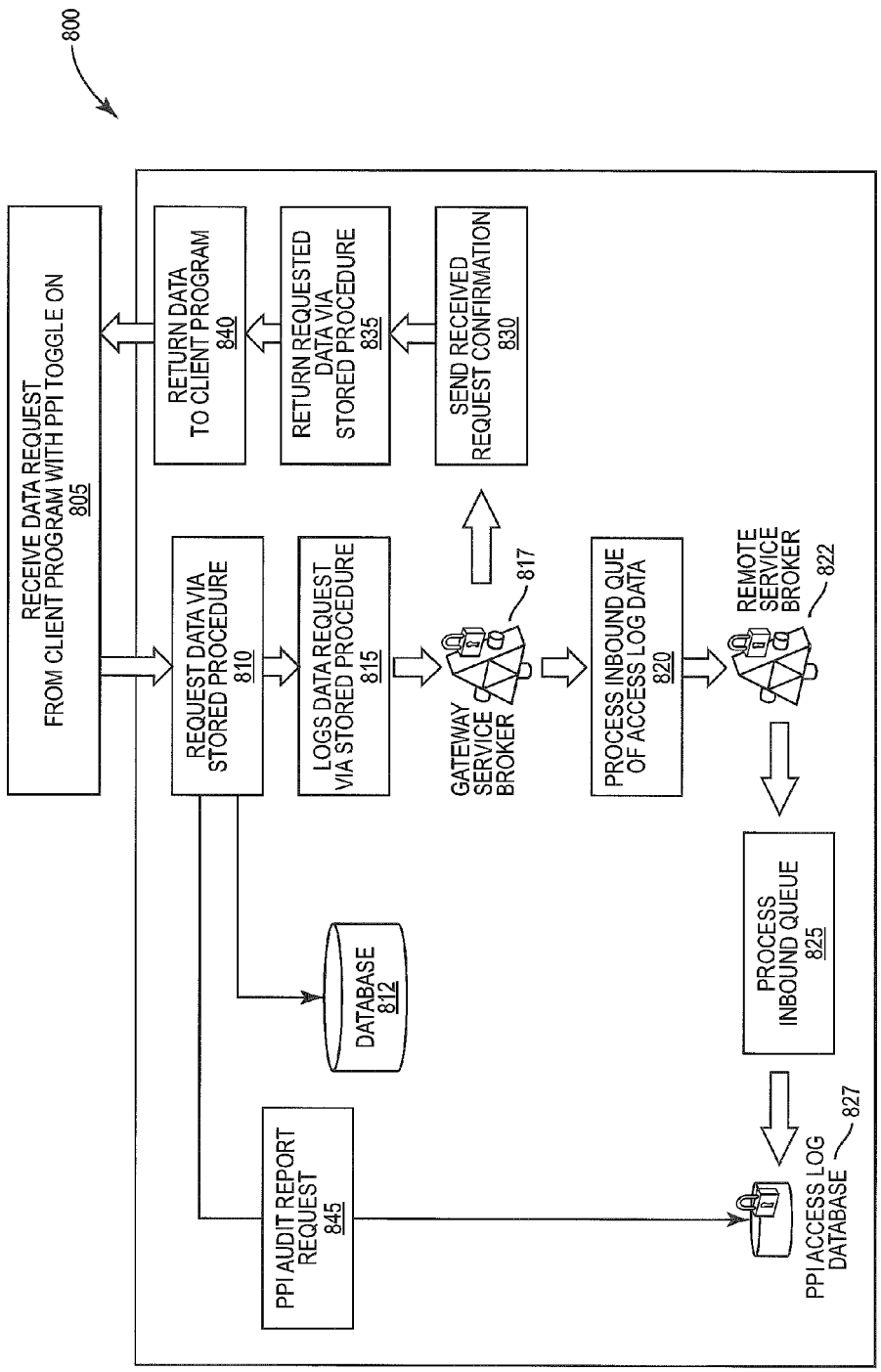
FIG. 8 is a diagram illustrating dataflow in a system for controlling access to protected personal information according to an exemplary embodiment of the present invention.

FIG. 8 is a diagram illustrating dataflow in a system for controlling access to protected personal information according to an exemplary embodiment of the present invention. It is assumed that access to protected personal information has been activated. As can be seen from FIG. 8, in block 805 a data request is received from a client program. In block 810, the requested data is retrieved, via a stored procedure, from a database 812. In block 815, the data request is logged via a stored procedure and information about the data request is sent to a secure gateway service broker 817. The gateway service broker 817 receives the information about the data request and, in block 820, processes an inbound queue of access log information. The queue of access log information is transmitted to remote service broker 822. Remote service broker 822 receives the access log data and, in block 825, the inbound queue of access log data is processed and information about the queue of access log data is stored in a PPI access log database 827.

Returning to gateway service broker 817, in block 830, confirmation is sent confirming that the data request has been received. In block 835, the requested data is returned via a stored procedure. In step 840, the data returned in response to the data request is returned to the client program that initiated the data request in block 805.

Returning to block 805, a data request received from a client program may be a request for protected personal information access log data stored in PPI access log database 827. In block 845, the requested log data is retrieved, via a stored procedure, from database 827. The requested log data is then transmitted to the user via gateway service broker 817.

Figure 9:
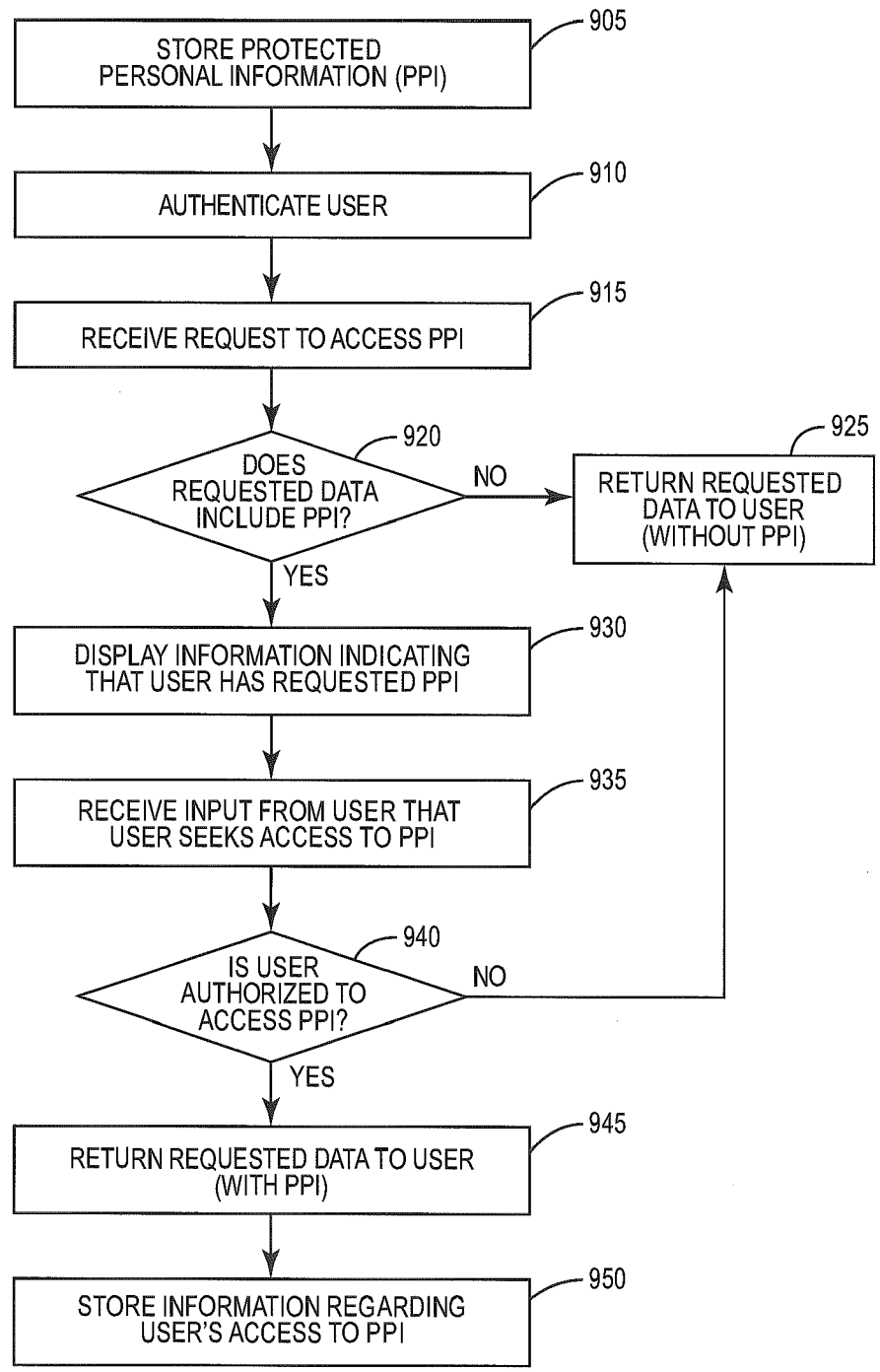
FIG. 9 is a diagram illustrating processing logic for a system for controlling access to protected personal information according to an exemplary embodiment of the present invention.

FIG. 9 is a diagram illustrating the logic for a process for a system for controlling access to protected personal information according to an exemplary embodiment of the present invention. As shown in FIG. 9, in block 905, the process stores protected personal information in a computerized database management system. Processing control is then transferred to block 910. In block 910, the process authenticates a user in response to request from the user. Processing control is then transferred to block 915. In block 915, the process receives a request to access information stored in the database and processing control is transferred to block 920. In block 920, the process determines whether the requested information includes protected personal information. If the requested information does not include protected personal information, processing control is transferred to block 925. In block 925, the process causes the requested information to be transmitted to the requesting user.

Returning to block 920, if the process determines that the requested data does include protected personal information, processing control is transferred to block 930. In block 930, the process displays information indicating that the data requested by the user includes protected personal information. Processing control is then transferred to block 935. In block 935, the process receives input from the user indicating that the user seeks access to the protected personal information included in the requested data. Processing control is then transferred to block 940. In block 940, the process determines whether the user is authorized to access protected personal information. If the process determines that the user is not authorized to access protected personal information, processing control is return to block 925, where the process causes the requested information to be transmitted to the requesting user. As can be appreciated, because the user was not authorized to access protected personal information, the data returned to the user does not include any protected personal information.

Returning to block 940, if the process determines that the user is authorized to access protected personal information, process control is transferred to block 945. In block 945, the process causes the requested information to be transmitted to the requesting user. Because the user was authorized to access protected personal information, the data returned to the user includes protected personal information. Processing control is then transferred to block 950. In block 950 process causes information about the protected personal information accessed by the user to be stored, for example, in a database management system. Information stored in the database management system regarding the user's access to protected personal information is discussed in more detail above.

Figure 10:
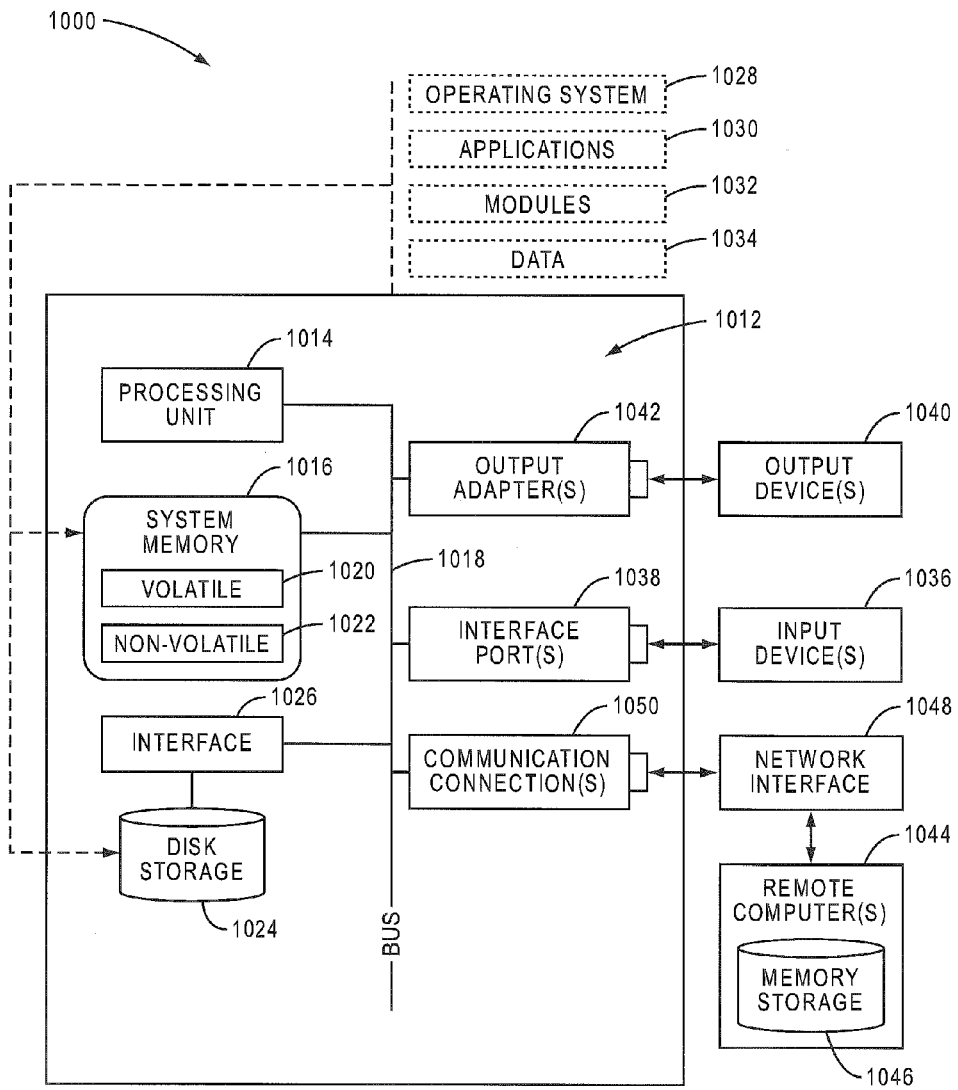
FIG. 10 is a diagram illustrating exemplary computer hardware and software to implement an embodiment of the invention.

FIG. 10 is a diagram illustrating exemplary computer hardware and software to implement an embodiment of the invention. Referring to FIG. 10, an exemplary environment 1000 for implementing various aspects of the invention includes a computer 1012, which includes a processing unit 1014, a system memory 1016, and a system bus 1018. The system bus 1018 couples the system components including, the system memory 1016 to the processing unit 1014. The processing unit 1014 can be any of various processors available. The system bus 1018 can be any of the available types of bus structures using any variety of available bus architectures. The system memory 1016 includes volatile memory 1020 and nonvolatile memory 1022.

Computer 1012 also may include removable/nonremovable, volatile/nonvolatile computer storage media, for example, a disk storage 1024. Disk storage devices 1024 may be connected to the system bus 1018 via removable or non-removable interface 1026.

FIG. 10 also illustrates software that allows interaction between users and computer resources, which may include an operating system 1028. System applications 1030 are allocated resources by operating system 1028 through program modules 1032 and program data 1034 stored either in system memory 1016 or on disk storage 1024. Aspects of the present invention may be implemented with various operating systems or combinations of operating systems.

A user enters commands or information into computer 1012 through input devices 1036, which connect to processing unit 1014 through the system bus 1018 via interface ports 1038. Input devices may include computer mice, touch screens, keyboards, scanners, etc., which can be used to input data. Output devices 1040 use some of the same type of ports as input devices 1036. Output adapter 1042 may be provided because some output devices 1040 like monitors, speakers and printers require special adapters. Other devices and/or systems of devices provide both input and output capabilities such as remote computers 1044.

Computer 1012 can operate in a networked environment using logical connections to one or more remote computers, such as remote computers 1044. The remote computers 1044 can be a personal computer, a server, a router, a network PC, a workstation, a microprocessor based appliance, a peer device or other common network node, which may include many or all of the elements of computer 1012. While only a single memory storage device 1046 is shown, remote computers 1044 may be logically connected to computer 1012 through a network interface 1048 and physically connected via communication connection 1050.

Although the present invention has been described with exemplary embodiments, it is to be understood that modifications and variations may be utilized without departing from the spirit and scope of the invention, as those skilled in the art will readily understand. Such modifications and variations are considered to be within the purview and scope of the appended claims and their equivalents.

We claim:

1. A computer implemented method of controlling access to protected personal information by a user of an information management application program that has access to the protected personal information, the method comprising:
   storing in a computer memory the protected personal information that is accessible by the information management application program;
   authenticating the user of the information management application program;
   receiving a first request from the authenticated user to access information accessible by the information management application program;
   determining whether the information requested by the user is comprised of the protected personal information;
   if the information requested by the user is comprised of the protected personal information, displaying information indicating that the information requested by the user is comprised of the protected personal information, but not displaying the requested protected personal information;
   in response to displaying information indicating that the information requested by the user is comprised of the protected personal information, receiving from the user input requesting access to the protected personal information;
   determining whether the user is authorized to access the requested protected personal information;
   if the user is authorized to access the requested protected personal information, displaying the requested protected personal information to the user;
   storing information i) indicating that the user accessed the requested protected personal information, and ii) identifying the protected personal information accessed by the user;
   providing a graphical user interface for receiving user input requesting access to the protected personal information; and
   displaying a button via the graphical user interface for receiving user input via a user input device for toggling between a first state in which protected personal information is not accessible to the user through search and display capabilities and a second state in which protected personal information is accessible to the user through search and display capabilities.

2. The method of claim 1, wherein displaying the button is further comprised of:
   displaying information indicating whether protected personal information is being displayed via the graphical user interface.

3. The method of claim 1, wherein the information management application program is a health care information management application program or an insurance claim information management application program and the protected personal information is comprised of protected health information.

4. The method of claim 3, wherein the protected health information is at least one item of information selected from a group consisting of Name, Address, Social Security Number, Medical Record Number, and Cardholder Identifier.

5. The method of claim 3, wherein the protected health information is at least one item of information selected from a first group consisting of Name, Address, Social Security Number, Medical Record Number, and Cardholder Identifier, and one or more items selected from a second group consisting of Date of Birth, Sex, Relationship (to cardholder), Diagnosis Code, National Drug Code (NDC), NDC Description, Generic Code Number (GCN), GCN Description.

6. The method of claim 1, wherein storing information indicating that the user accessed the requested protected personal information is further comprised of storing information identifying one or more items of information selected from a group consisting of: Information Viewed or Accessed; Date and Time of View or Access User Name, User Identifier, Application Program, Insurance Carrier Name, Insurance Carrier Identifier, Insurance Plan Name, Insurance Plan Identifier, Insurance Group, Store Group Identifier, National Council for Prescription Drug Programs (NCPDP) or National Provider Identifier (NPI) Quantity Dispensed, Days Supply, Prescription Number, Fill Date, Coordination of Benefits (COB).

7. The method of claim 1, wherein the information management application program is a financial information management application program and the protected personal information is comprised of financial information.

8. The method of claim 1 further comprising:
   in response to receiving from the user input requesting access to the protected personal information and determining that the user is authorized to access the requested protected personal information, storing information indicating that the user has requested access to and is authorized to access protected personal information for use in responding to the user's next request for information.

9. The method of claim 8, further comprising:
   receiving a second request from the authenticated user to access information accessible by the information management application program;
   if the information requested by the user is comprised of protected personal information, displaying the protected personal information without requiring further user input requesting access to the protected personal information.

10. The method of claim 8, further comprising:
    receiving input from the user via the user input device indicating that displayed protected personal information should be concealed;
    in response to receiving the input that displayed protected personal information should be concealed, concealing the previously displayed protected personal information.

11. The method of claim 10, further comprising:
    in response to receiving from the user input requesting that displayed protected personal information should be concealed, storing information indicating that the user has requested that protected personal information be concealed for use in responding to the user's next request for information.

12. The method of claim 11, further comprising:
    receiving a third request from the authenticated user to access information accessible by the information management application program;
    if the information requested by the user is comprised of protected personal information, concealing the protected personal information without requiring further user input requesting that the protected personal information be concealed.

13. A system, comprising:
a processor; and
a memory coupled to the processor, wherein the memory comprises program instructions executable by the processor to implement an information management application program that has access to protected personal information and to control access to the protected personal information by a user of the information management application program, wherein the information management application program is configured to:
store the protected personal information that is accessible by the information management application program;
authenticate the user of the information management application program;
receive a request from the authenticated user to access information accessible by the information management application program;
determine whether the information requested by the user is comprised of the protected personal information;
if the information requested by the user is comprised of the protected personal information, display information indicating that the information requested by the user is comprised of the protected personal information, but not display the requested protected personal information;
in response to the display of information indicating that the information requested by the user is comprised of the protected personal information, receive from the user input requesting access to the protected personal information;
determine whether the user is authorized to access the requested protected personal information;
if the user is authorized to access the requested protected personal information, display the requested protected personal information to the user;
store information i) indicating that the user accessed the requested protected personal information, and ii) identifying the protected personal information accessed by the user;
provide a graphical user interface for receiving user input requesting access to the protected personal information; and
display a button via the graphical user interface for receiving user input via a user input device for toggling between a first state in which protected personal information is not accessible to the user through search and display capabilities and a second state in which protected personal information is accessible to the user through search and display capabilities.

14. A computer-readable non-transitory storage medium, comprising program instructions configured to implement an information management application program that has access to protected personal information and to control access to the protected personal information by a user of the information management application program, wherein the information management application program is configured to:
store the protected personal information that is accessible by the information management application program;
authenticate the user of the information management application program;
receive a request from the authenticated user to access information accessible by the information management application program;
determine whether the information requested by the user is comprised of the protected personal information;
if the information requested by the user is comprised of the protected personal information, display information indicating that the information requested by the user is comprised of the protected personal information, but not display the requested protected personal information;
in response to the display of information indicating that the information requested by the user is comprised of the protected personal information, receive from the user input requesting access to the protected personal information;
determine whether the user is authorized to access the requested protected personal information;
if the user is authorized to access the requested protected personal information, display the requested protected personal information to the user; store information i) indicating that the user accessed the requested protected personal information, and ii) identifying the protected personal information accessed by the user;
provide a graphical user interface for receiving user input requesting access to the protected personal information; and
display a button via the graphical user interface for receiving user input via a user input device for toggling between a first state in which protected personal information is not accessible to the user through search and display capabilities and a second state in which protected personal information is accessible to the user through search and display capabilities.

* * * * *